United States Patent [19]
Campbell et al.

[11] Patent Number: 5,791,497
[45] Date of Patent: Aug. 11, 1998

[54] METHOD OF SEPARATING FRUIT OR VEGETABLE PRODUCTS

[75] Inventors: Duncan Campbell, Central Point; H. Parks Squyres, Medford, both of Oreg.

[73] Assignee: SRC Vision, Inc., Medford, Oreg.

[21] Appl. No.: 647,017

[22] Filed: May 8, 1996

[51] Int. Cl.⁶ .................................................. B07C 5/00
[52] U.S. Cl. ........................................ 209/577; 209/587
[58] Field of Search .................................. 209/577, 587, 209/576, 580, 581

[56] References Cited

U.S. PATENT DOCUMENTS

| | | | |
|---|---|---|---|
| 4,738,175 | 4/1988 | Little et al. | 83/71 |
| 5,085,325 | 2/1992 | Jones et al. | 209/580 |
| 5,440,127 | 8/1995 | Squyres | 250/341.8 |
| 5,443,164 | 8/1995 | Walsh et al. | 209/580 |
| 5,464,981 | 11/1995 | Squyres et al. | 250/341.8 |

*Primary Examiner*—David H. Bollinger
*Attorney, Agent, or Firm*—Stoel Rives LLP

[57] ABSTRACT

A method of separating selected fruit from a volume of fruit is based on the reflectivity of the selected fruit. The method utilizes an automated optical inspection and sorting system to illuminate a volume of fruit including cranberries characterized by a spectral power distribution in the infrared spectral region. The system detects reflections of wavelengths of the illumination in the infrared spectral region, identifies the selected fruit based on the detected reflectivity, and sorts the selected fruit from the volume of fruit.

12 Claims, 7 Drawing Sheets

METHOD OF SEPARATING FRUIT OR VEGETABLE PRODUCTS

TECHNICAL FIELD

The present invention pertains to a method of operating automated optical inspection and sorting systems and, in particular, to methods for operating such systems to separate selected fruits or vegetables from a large group of produce.

BACKGROUND OF THE INVENTION

Automated optical inspection and sorting systems have been used to inspect and sort various target specimens including fruits and vegetables, processed meats, baked goods, and other foodstuffs; to separate different types of recyclable material; and to sort foreign or defective items from supplies of wood chips. These systems typically employ video cameras with photo detector arrays to acquire images of target specimens moved on a conveyor belt across an optical scanning area. Illumination of the specimens is generally provided by broad-spectrum tubular fluorescent lamps of the type described in U.S. Pat. No. 5,440,127. Signal processing circuitry identifies variations in the shade of target specimen images and sorts target specimens accordingly.

In the commercial harvesting of produce, such as cranberries, it is necessary to separate unacceptable berries from the acceptable berries. There are several types of defective cranberries that are difficult to detect when the fruit is picked and sorted in large volumes. The most notable of these is a berry that has a dark red color and is soft to the touch. This is due to rot caused by either bacterial infection or bruising. Another type of defective berry is a white berry that has a smooth outer skin like that of good fruit but which is compliant to the touch. The feel of this defective berry is like that of an inflated balloon. These defective berries are called "balloons" or "poppers." The compliancy may be due to a gaseous build up within the sealed outer skin produced as a by-product of bacterial action. Yet another defective berry is one that is deep red in color but which has been infected with a bacterium that makes the fruit fluoresce at 680 nm when illuminated with long-wave ultraviolet light in the region of 350 nm to 400 nm.

It is desirable for health reasons as well as for consumer acceptance to remove rotten or defective cranberries from a volume to be shipped to consumers. It is also desirable to remove defective cranberries from the shipment so that they may be sold commercially on the basis of weight and/or volume.

A number of techniques have been developed over the years to remove a defective product from an incoming harvest stream. The most notable of these is a technique that depends upon the coefficient of restitution of acceptable fruit. This technique consists of dropping the fruit vertically onto an angled wooden board. The good ripe fruit with the correct coefficient of restitution will bounce over a low barrier placed just below the trajectory of acceptable fruit. Fruit that is seriously defective will not bounce over the barrier and will be rejected. Large numbers of these devices are employed to detect defects, but the technique is not 100 percent effective and thus other methods must be employed.

Another method of detecting defective fruit consists of manual and/or machine inspection of fluorescence of the fruit induced by illumination with ultraviolet light. Only fruit infected with a certain bacterium that exhibits such fluorescence can be detected with this method. The fluorescence induced is at a very low level, and the manual inspectors must work in a darkened room so that their eyes can become adapted to the dark. Certain wavelengths of ultraviolet light have ionizing potential and may cause adverse long-term effects on inspectors, such as the development of cataracts on the eye. Also, it is difficult to produce a machine that reliably detects such low levels of fluorescence. These machines do not have wide industry acceptance due to their limited detection capabilities.

The most reliable techniques have been those developed by the manual inspectors. They have developed a sense of what is defective depending on a number of visual and tactile clues not easily described or taught. One technique consists of rolling the fruit over a firm surface with the palm and fingers of their hands to feel the firmness of the berry. Another technique consists of a simple visual inspection of the shininess and texture of the surface of the fruit under glancing light conditions. However, these manual techniques are not practical for commercial production purposes.

In the production of food products, it is sometimes desirable to separate good red berries from good white berries. Good ripe cranberries are dark red in color and are firm to the touch. This ripe fruit is packaged for the consumer, squeezed for juice, or jelled and canned. During certain periods of the harvest, white or pink berries are used only for the production of fruit juices and are not packaged for direct use by the consumer. This is so because consumers are most familiar with dark red cranberries and most likely would not accept white or pink berries for use. Current inspection and separating systems for separating white or pink berries from red berries are not practical for large scale commercial fruit production.

SUMMARY OF THE INVENTION

An object of the present invention is, therefore, to provide a method of operating an automated optical inspection and sorting system so that it can effectively identify and separate selected produce from a large volume of produce.

Another object is to provide a method of operating an automated optical inspection and sorting system so that it can effectively identify and sort produce that has a ruined or diminished chlorophyll reflectivity.

Yet another object is to provide a method of operating an automated optical inspection and sorting system so that it can effectively identify and sort selected cranberries from a large volume of ripe cranberries.

Another object is to provide a method of operating an automated optical inspection and sorting system so that it can effectively sort defective cranberries that have been subject to rot either by bacterial infection or bruising from a large volume of acceptable cranberries.

Yet another object is to provide a method of operating an automated optical inspection and sorting system so that it can effectively sort defective cranberries having a gaseous build up produced as a by-product of bacterial action.

A further object is to provide a method of operating an automated optical inspection and sorting system so that it can effectively sort cranberries that appear to be good but have been infected with bacteria.

Still another object is to provide a method of operating an automated optical inspection and sorting system so that it can effectively sort white and/or pink cranberries to be used only for fruit juice from red ripe cranberries to be sold for consumer use.

The present invention is a method of identifying and separating from a volume of acceptable produce defective produce, such as cranberries, that have been subject to rot or bacterial infection. This method uses an automated optical inspection and sorting system to identify and separate the defective cranberries from the good, ripe cranberries. It has been found that rotten or bacterially infected cranberries share a common characteristic that is not present in good cranberries. That is, defective cranberries contain chlorophyll whose reflectivity of light in the near infrared region of the electromagnetic spectrum is ruined or diminished by rot or bacterial infection. The optical inspection and sorting system utilizes differences in reflectivity between good cranberries and defective cranberries at wavelengths in the near infrared portion of the electromagnetic spectrum. The system identifies the defective cranberries and separates them from a volume of good ripe cranberries. Such a system is operated by illuminating a monolayered mixture of good cranberries and defective cranberries with illumination in the near infrared portion of the electromagnetic spectrum. The optical inspection and sorting system includes a camera having a spectral sensitivity set to identify the defective cranberries by their relatively low reflectivity of the illumination. The defective cranberries are then sorted from the good cranberries.

The present invention is also a method of using the optical inspection and sorting system to separate white and/or pink berries that are to be used only for fruit juice from ripe red berries that are to be sold directly to the consumer. The optical inspection and sorting system utilizes differences in reflectivity between white and/or pink cranberries and ripe red cranberries at wavelengths in the visible portion of the electromagnetic spectrum. The system identifies the white and/or pink cranberries and separates them from a volume of good, ripe red cranberries. The system is operated by illuminating a monolayered mixture of ripe red cranberries and white and/or pink cranberries with illumination in the visible portion of the electromagnetic spectrum. The optical inspection and sorting system includes a camera sensitive to the visible portion of the electromagnetic spectrum to identify the white and/or pink cranberries by their relatively high reflectivity of the illumination. These cranberries are then sorted from the red ripe cranberries.

Additional objects and advantages of the present invention will be apparent from the following detailed description of preferred embodiments thereof, which proceeds with reference to the accompanying drawings.

DETAILED DESCRIPTION OF PERFERRED EMBODIMENTS

Figure 1:
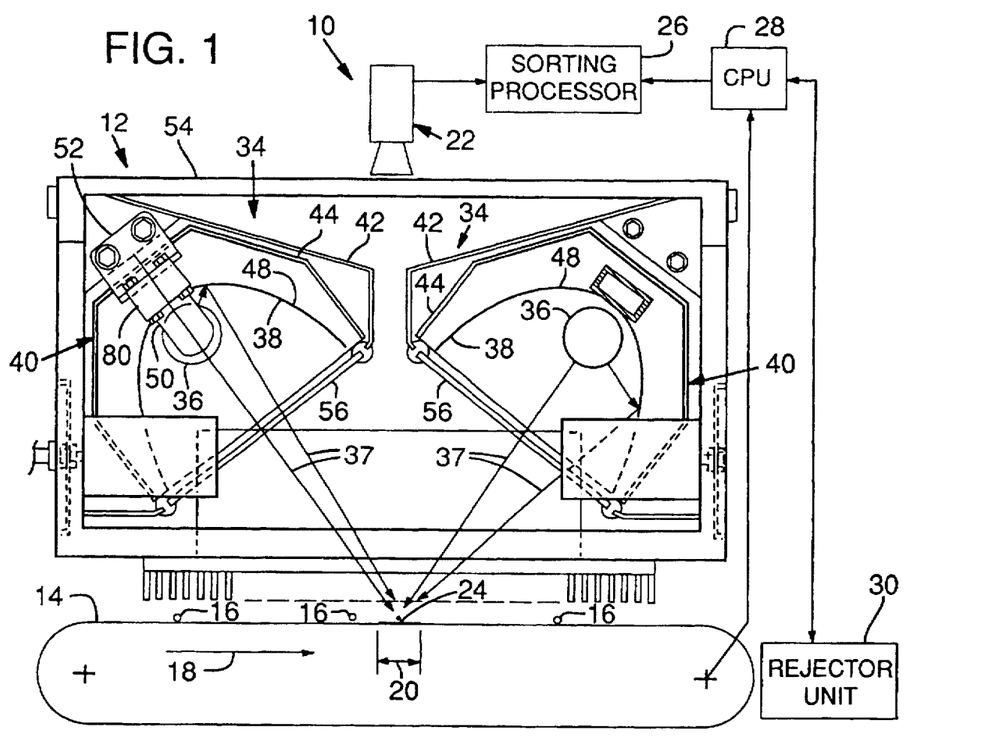
FIG. 1 is a schematic diagram showing a side elevation view of an on-belt optical inspection system operable in accordance with the present invention.
Figure 2:
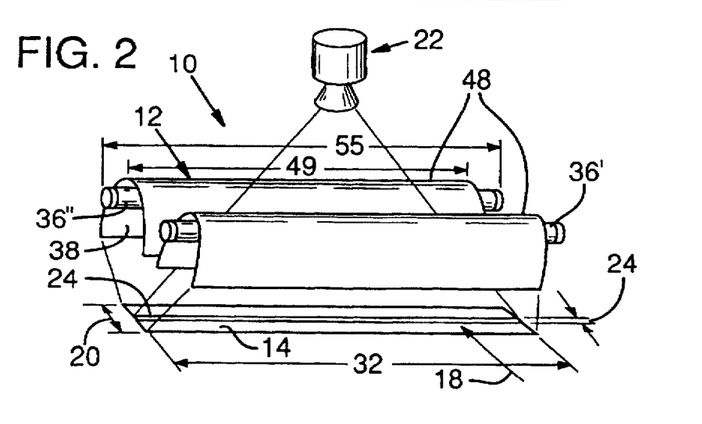
FIG. 2 is an isometric view of the illumination system shown in FIG. 1, with parts removed for clarity.

FIGS. 1 and 2 show an automated optical inspection system 10 suitable for carrying out a method according to the invention. Inspection system 10 may be of the on-belt specimen inspection and sorting type described in U.S. Pat. No. 4,738,175 to Little et al. for a DEFECT DETECTION SYSTEM and U.S. Pat. No. 5,085,325 to Jones et al. for a COLOR SORTING SYSTEM AND METHOD, both assigned to the assignee of the instant application and incorporated herein by reference.

Inspection system 10 includes an illumination system 12 and employs an endless conveyor belt 14 having a width of about 1.2 meters (48 inches) to move target specimens 16 in a direction 18 across an illumination area 20. Inspection system 10 sorts and separates target fruit or vegetable specimens 16, such as cranberries, that are moved by conveyor belt 14 as quickly as about 2.5–3.0 m/sec. (500–600 ft./min.) across illumination area 20. To prevent the berries from rolling around on the belt, a product stabilizer (not shown) may be employed to contact the berries as they pass beneath it. Such stabilizers are known in the art and are generally in the form of a cylindrical roller constructed of an inflatable airtight bladder of pliable material to conform to various types of products that are placed on the belt. A product stabilizer of this type is described in U.S. Pat. No. 5,085,325 to Jones et al. Alternatively, a belt having a knobbed surface (not shown) may be employed so that the berries are located and held stationary between the knobs. One example of such a belt is the A-5 profile, manufactured by Ammeraal International BV, located at Handelsstraat 1, Postbus 38, 1700 AA Heerhugowaard, Holland.

A high-resolution tri-linear line scan video camera 22 scans specimens 16 as they pass through a scanning area 24 within illumination area 20. A scan is completed once each millisecond. Camera 22 uses a silicon detector that is compatible with other system parameters, such as belt speed and illumination intensity. The camera 22 has three arrays of photosensors each of which receives light reflected from discrete locations or pixels along a scan line extending in a direction generally perpendicular to the movement of the belt 14. The scan lines are located about 112 microns apart on the array which are about 0.475 cm (0.187 in) apart in the direction of movement of the belt. Camera 22 acquires data representative of the light reflectivity of target specimens 16. It samples the intensity of light reflected by specimens 16 and the belt 14 and assigns a brightness value for each pixel. The brightness values are determined by the spectral power distribution of the illumination, the spectral response of specimens 16, the spectral response of belt 14, and the spectral response of camera 22. Camera 22 provides 2048 pixels per scan line and resolves a distance of about 0.6 mm (0.023 in.) across belt 14 into one pixel. A range of about five to eight pixels is resolved into an image of a single cranberry. Camera 22 uses a lens with a focal length that images the full width of scanning area 24 onto the full width of the camera pixel array. Preferably, the memory of camera 22 has sufficient capacity to store the data from thirty-two scan lines. A sorting processor 26 processes the image data generated by camera 22. A central processor unit 28 linked with sorting processor 26, conveyor belt 14, and a rejector unit 30 synchronizes the timing of the position of target specimens 16 to the operation of rejector unit 30. Rejector unit 30 sorts and separates specimens 16 when sorting processor 26 determines that they include certain selected physical features such as low spectral reflectance or absorption. Even though only one camera is shown, skilled persons will understand that more than one camera unit may be used. For example, two side-by-side lower-resolution cameras may be employed.

Illumination system 12 includes multiple, preferably two, light source assemblies 34 positioned to project electromagnetic radiation or illumination across the width of belt 14 at scanning area 24 in illumination area 20. Each light source assembly 34 includes one or two nonfluorescing rare gas discharge lamps 36 for emitting respective high-intensity light rays 37 of select wavelengths. These lamps are of the type described in U.S. Pat. No. 5,440,127 to Squyres for METHOD AND APPARATUS FOR ILLUMINATING TARGET SPECIMENS IN INSPECTION SYSTEM, assigned to the assignee of the present invention and herein incorporated by reference.

Light rays 37 reflect off an inner light-reflecting surface 38 of a shroud-like reflector structure 40 and are directed toward illumination area 20. The lamps 36 are cooled by forced air.

Reflector structure 40, which fits within and is supported by an outer covering 42 of light source assembly 34, includes a housing 44 and a preferably hemi-elliptical reflector 48 secured within housing 44. Each of lamps 36 may be held in place by, for example, a pair of tube sockets 50 that are supported by a light source support member 52 connected to frame 54. The length 55 of each lamp 36 is generally a function of and typically greater than length 32 of scanning area 24.

Each lamp 36 is positioned within rectangular frame 54 so that it lies in a direction generally perpendicular to conveyor belt travel direction 18 to illuminate target specimens 16 as they are scanned by video camera 22. Light rays 37 propagate directly toward illumination area 20. Light rays 37 also propagate toward and reflect from light-reflecting surface 38 of hemi-elliptical reflector 48 toward illumination area 20. Hemi-elliptical reflectors 48 have lengths 74 that are about equal to length 32 of scanning area 24 and about equal to or shorter than length 55 of lamps 36. Because reflectors 48 are of hemi-elliptical shape, they produce a line focus of light rays that strike illumination area 20 and scanning area 24 on conveyor belt 14.

Lamps 36 also typically have a smaller diameter than conventional broadspectrum fluorescent tubes. When used with hemi-elliptical reflectors, smaller diameter lamps come closer to approximating a line source of illumination than larger diameter lamps. Line sources are more efficient than diffuse sources of illumination.

Preferably, an optically transmissive protective covering 56 encloses reflector structure 40 to protect target specimens 16 from debris falling from a broken lamp 36. Also, hemi-elliptical reflector 48 supports a preformed aluminum substrate that carries on its inner surface 38 a light-reflective coating such as, for example, the "BV2 coating" having 89 to 93 percent reflectivity, which is produced by Optical Coating Labs, Inc. of Santa Rosa, Calif.

Figure 3:
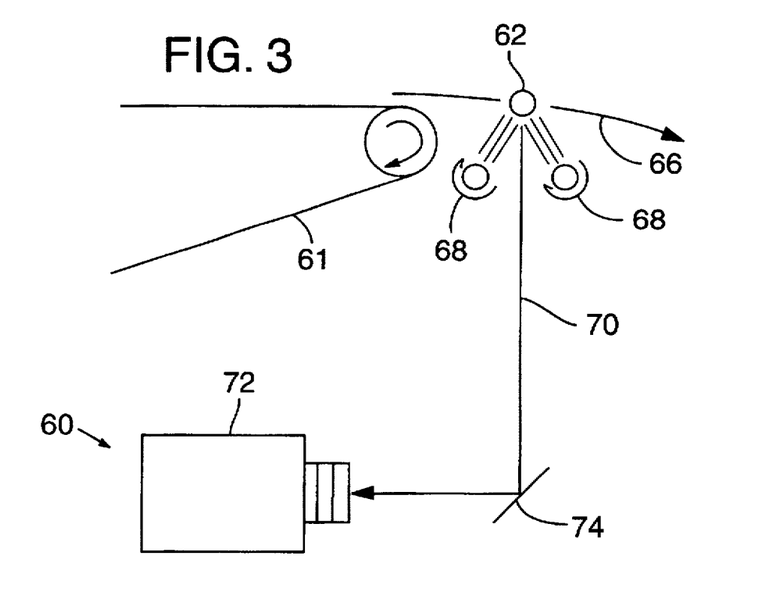
FIG. 3 is a schematic diagram showing a fragmentary side elevation view of an off-belt optical inspection system operable in accordance with the present invention.

Although inspection system 10 is shown as an on-belt inspection system, the methods of the invention can also be carried out with the use of off-belt inspection systems 60 such as the type seen in FIG. 3. This type of system utilizes an automated optical inspection system similar to the inspection system 10 of FIG. 1, but mounted beneath the belt 61. A specimen 62 is propelled from the belt 61 along a trajectory 66 toward an acceptance conveyor (not shown). Lamps 68 provided below the belt 61 illuminate the specimen 62 in mid-air. Light rays reflected from the specimen 62 generally travel along a path 70 and are seen by a camera 72 through an adjustable mirror 74. System 60 operates in a manner similar to system 10 in FIG. 1 to separate defective berries from acceptable berries.

In both the on-belt and off-belt systems, the selected physical features of the specimen form the bases for sorting decisions. These features are characterized by the optical response of specimens 16 including recognizable patterns of reflection and absorption of radiation. The optical response of a specimen 16 to radiation of a particular wavelength or range of wavelengths can signify defects such as the presence of rot or bacterial infection.

Each of lamps 36 contains a rare or noble gas or a mixture of rare gases. Each rare gas and each mixture of rare gases emits select wavelengths of high-intensity illumination when ionized at the breakdown voltage. Lamps 36 emit respective light rays 37 with an intensity approximately two to three or more times that of conventional fluorescent sources. The intensity of radiation reflecting from target specimens 16 depends on the distance between lamps 36 and target specimens 16. A particular rare gas or mixture of rare gases is chosen according to the specific intended application of inspection and sorting system 10. For example, since defective cranberries have ruined or diminished chlorophyll reflectivity in the infrared spectral range, it is preferable to use a gas or gas mixture that concentrates radiation in the infrared spectral range.

Figure 4:
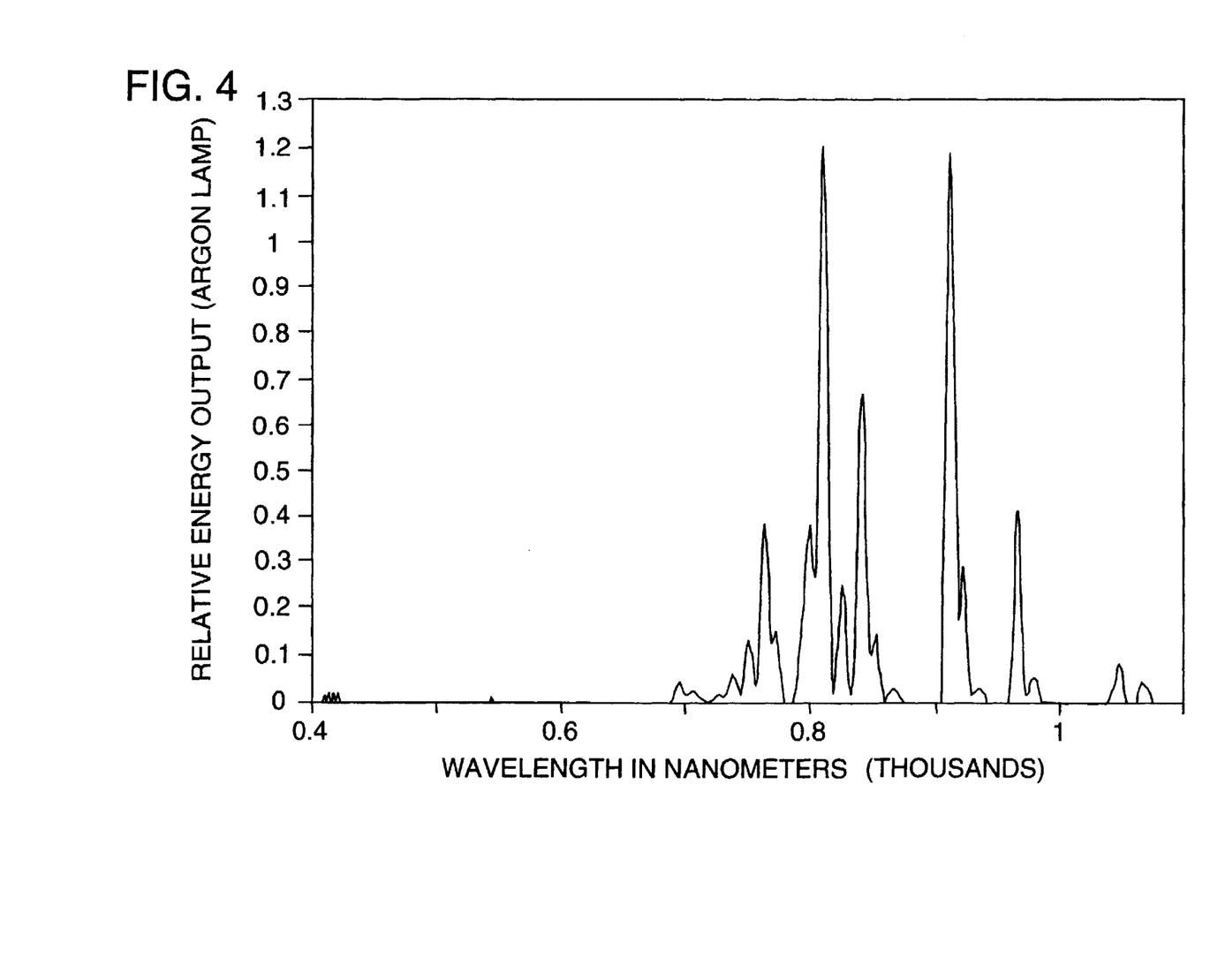
FIG. 4 presents a representation of the relative spectral power distribution of a lamp containing argon.

More specifically, when, for example, 20 mm diameter lamps 36 contain primarily argon at a pressure of 665 Pa (Newtons per square meter ($N/m^2$)) (approximately 5 Torr), they emit high-intensity radiation in the near infrared regions of the electromagnetic spectrum. As can be seen in FIG. 4, the range extends from approximately 700 nm to about 1100 nm with a major spikes at about 810 nm and 910 nm. This embodiment of lamps 36 is particularly well suited for inspecting and sorting defective cranberries infected with bacteria or rot from good ripe cranberries. Bacteria or rot ruins or substantially diminishes the typical chlorophyll reflectivity of an infected cranberry in the near infrared region of the electromagnetic spectrum. Good ripe cranberries are much more highly reflective in the infrared range than defective cranberries. Therefore, the inspection and sorting system 10 identifies defective cranberries by their comparatively low reflectivity and sorts them from the good cranberries.

Figure 5:
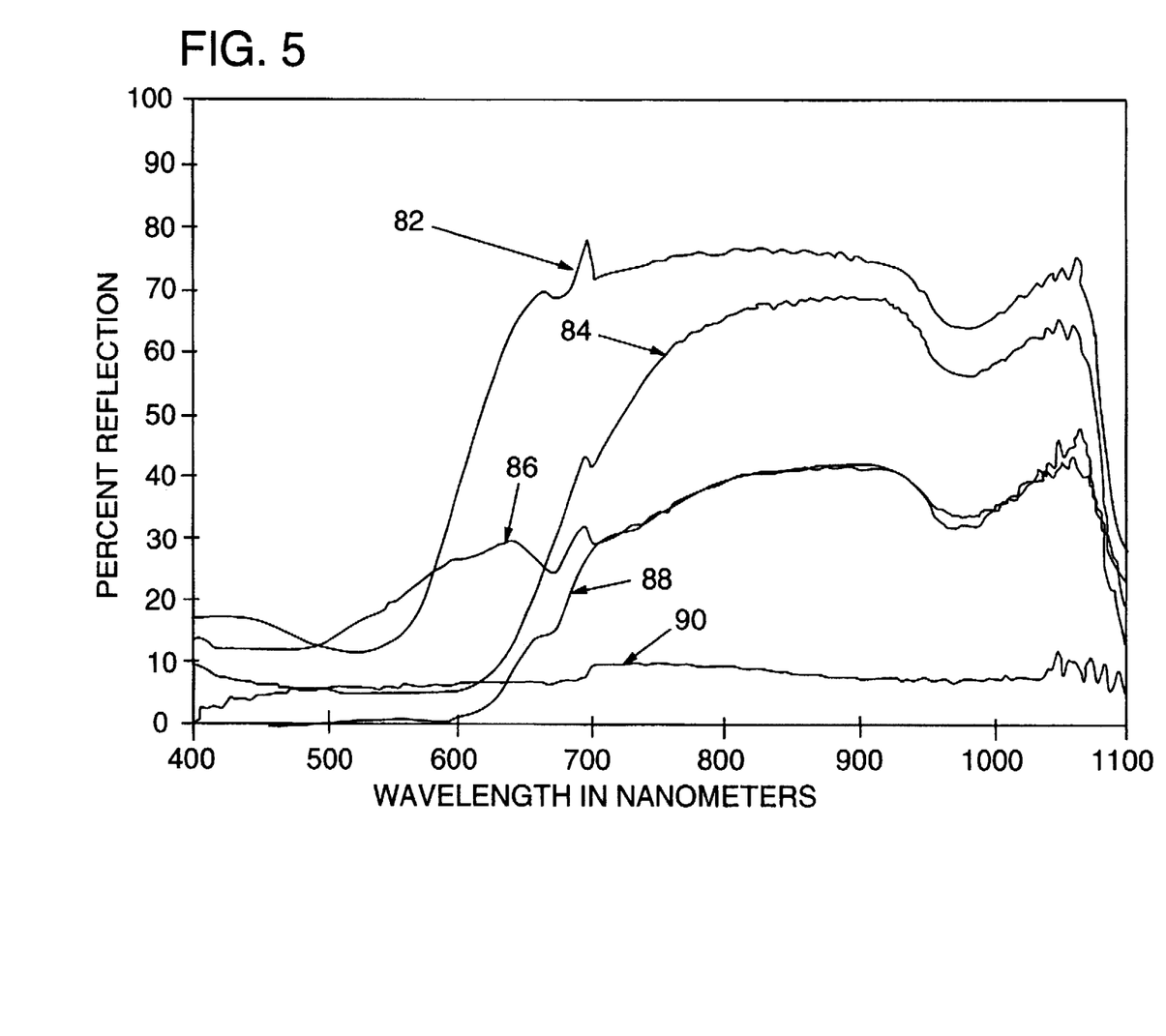
FIG. 5 shows as a function of wavelengths the comparative relationship of representative reflectivities of good white cranberries, good red cranberries, white cranberries with bacterial infection, dark red cranberries with rot, and dark black cranberries with rot.

FIG. 5 shows the comparative relationship of representative reflectivity curves of both good and defective cranberries. Curve 82 represents the reflectivity of good white cranberries, and curve 84 represents the reflectivity of good red cranberries. Curve 86 shows the reflectivity of white cranberries with bacterial infection. Curve 88 shows the reflectivity of red cranberries with rot, and curve 90 shows the reflectivity of black cranberries with rot. These reflectivity curves extend over a range of wavelengths of the electromagnetic spectrum from about 400 nm to about 1100 nm.

Most human eyes can detect electromagnetic radiation in a spectral range of about 380 nm to 700 nm but cannot detect electromagnetic radiation within the infrared spectral range that includes wavelengths of about 750 nm to about 1100 nm.

As a practical matter, automated optical inspection systems best distinguish good cranberries from defective cranberries when their reflectivities differ by as much as possible. Good cranberries and defective cranberries in a single shipment typically have variations in reflectivity that make it impractical to sort them with commercially acceptable accuracy when their reflectivities are too close in a given wavelength range. At wavelengths in the near infrared region, particularly at wavelengths between about 750 and about 1100 nm, good cranberries and defective cranberries have a particularly large difference in reflectivity.

Over a portion of the visible wavelength range (i.e., from about 400 nm to about 600 nm) both good and defective cranberries have relatively low reflectivities. At blue, green, and yellow wavelengths (e.g., from about 400 nm to about 580 um), good white cranberries (curve 82) and defective white cranberries (curve 86) have reflectivities of between 10 percent and 20 percent. At the same wavelengths, good red cranberries (curve 84) and defective black cranberries (curve 90) have reflectivities of between 0 percent and 10 percent while defective red cranberries (curve 88) have about 0 percent reflectivity. However, at wavelengths from the near infrared and extending into the far infrared region (e.g., from about 750 nm to 1100 nm), good cranberries, both red and white, have a much higher reflectivity than that of defective cranberries, which absorb light waves within this region. Beginning at the orange wavelength (e.g., about 600 nm), reflectivity curve 82 of good white cranberries increases sharply and remains substantially higher than the reflectivity curves of all other cranberries throughout the infrared range. At the wavelength of about 680 nm, reflectivity curve 84 of good red cranberries increases sharply and remains substantially higher than the reflectivity curves 86, 88, and 90 of defective cranberries throughout the infrared range. The difference of reflectivity between good cranberries, both white and red, and a defective cranberry is most pronounced between about 750 nm and about 1100 nm.

Some defective cranberries do have increased reflectivity approaching the far infrared range. For example, the reflectivity curve 86 of white cranberries infected with bacteria begins to rise at wavelengths of about 500 nm. Red cranberries with rot have increased reflectivity starting at wavelengths of about 620 nm as represented by curve 88. At about 700 nm reflectivity curves 86 and 88 substantially merge and reach a maximum reflectivity of just less than 50 percent at about 1007 nm. As seen by curve 90, black cranberries with rot have very little reflectivity throughout the entire shown spectral range.

The invention exploits those differences in reflectivity by illuminating a mixture of good cranberries and defective cranberries with light in the near infrared region. The light is used to identify the defective cranberries and to sort them from the mixture. Defective cranberries to be separated from the mixture include those that reflect less of the power of the illumination in the near infrared region than do good cranberries. Poor reflectivity indicates the presence of defects, such as bacterial infection or rot.

Figure 6:
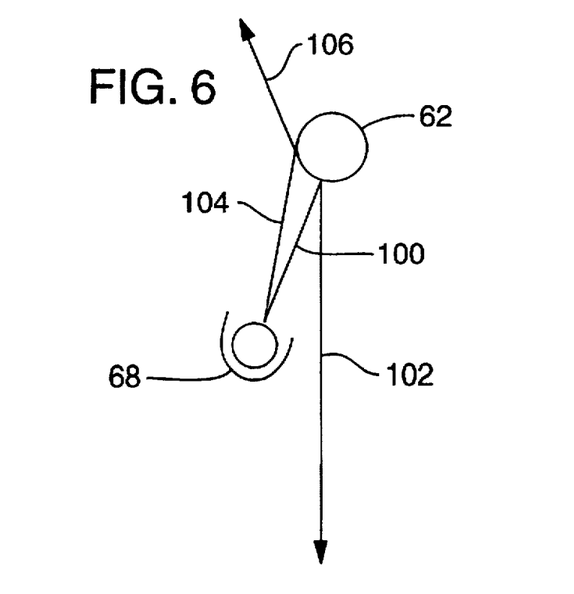
FIG. 6 is a schematic representation of light rays reflected from a cranberry.
Figure 7:
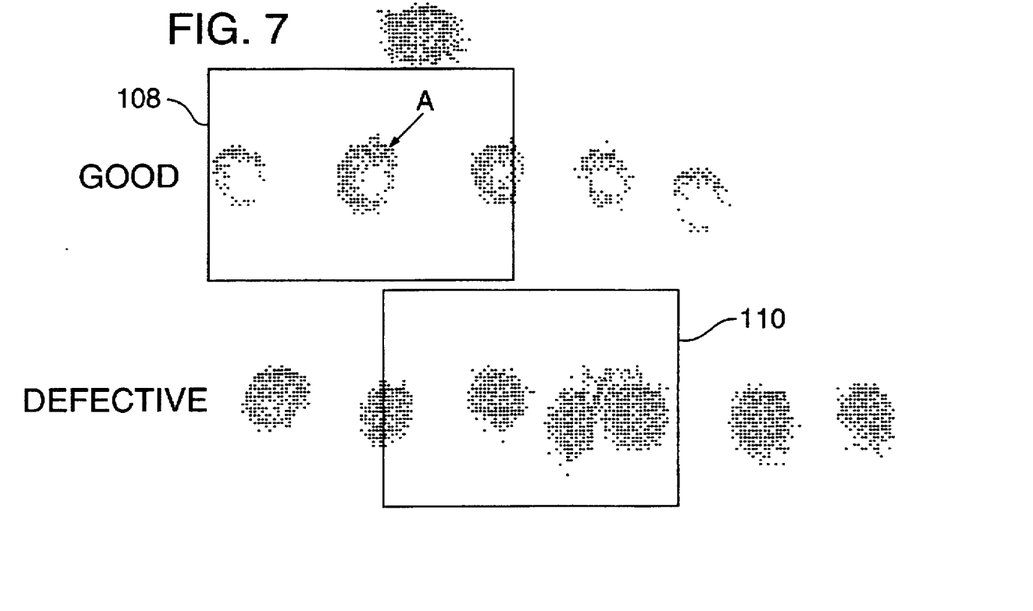
FIG. 7 is a pictorial representation of cranberry image data taken from various camera scans.
Figure 8:
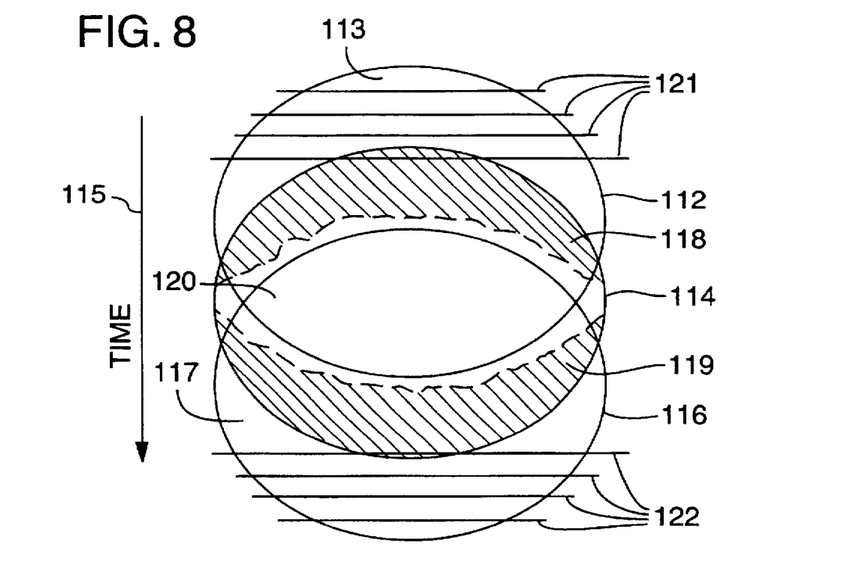
FIG. 8 is a schematic representation of three superimposed images of a berry at different points in time.

In some instances during illumination of the cranberries, not all of the reflected light rays are seen by the camera. For example, as shown in FIG. 6, some of the light rays 100 from the lamp 68 strike the berry 62, producing a spectral reflectance that travels along a path 102 that is within the field of view of the camera. Other light rays 104 strike the berry producing a reflectance that travels along a path 106 that is not viewed by the camera. The resulting image seen by the camera is one in which a crescent shaped "shadow" appears along the leading and trailing edges of the berry with a "hot spot" or bright portion in the center. The leading edge is the front edge of the berry in the direction of belt movement. The trailing edge is the edge of the berry opposite the leading edge. The "shadow" effect is diminished at the lateral edges of the berry due to elongated nature of the lamps along an axis perpendicular to belt movement. This "shadow" effect is best seen in FIGS. 7 and 8. For example, in FIG. 7, good berries are seen in camera image frame 108. However, the "shadow" around berry A causes the processor 26 to declare it a defective berry even though it is good. Bad or defective berries are seen in camera image frame 110. It is understood that the berries do not actually cast a shadow in the normal sense of the word. The term "shadow" is used here to refer to a dark region that is seen by the camera due to its inability to see all of the reflected light.

The "shadow" may be eliminated by diffusing the light with diffusers or by further separating the lamps to "kick up" the leading and trailing edges while diminishing the central "hot spot." Diffusing the light or further separating the lamps will cause the light to reflect differently from the berry so that more of the reflected light is seen by the camera. However, a more effective method of eliminating the "shadow" is by edge erosion or spatial filtering, which may be performed within the memory of the processor 26, within the memory of the camera, or any number of other ways known to those skilled in the art. One example of an apparatus that performs edge erosion is described in U.S. Pat. No. 5,443,164 to Walsh et al. for PLASTIC CONTAINER SORTING SYSTEM AND METHOD, assigned to the assignee of the present invention and incorporated herein by reference.

Elimination of the "shadow" can best be described with reference to FIG. 8. For example, camera 22 has the capability of taking three simultaneous images 112, 114, and 116 of belt 14 as a berry passes through the scanning area 24. These images overlap and are stored within either the camera memory or the processor memory. Image 114 represents the position of a berry traveling on the belt in the direction of arrow 115. Image 112 has a portion 113 that does not intersect image 114 and which represents a portion of the belt behind or trailing the berry. Likewise, image 116 has a portion 117 that does not intersect image 114 and which represents a portion of the belt in advance of the berry. Images 112 and 116 intersect within image 114 to form a section 120 which is the optimum portion of the berry to measure light reflectivity. The "shadow" portions 118,and 119 are seen at the trailing and leading edges of image 114 of the berry. Preferably, the data are read from the memory in such a way as to misalign the images 112, 114, 116 so that the first four scan lines 121 of image 112 replace the trailing "shadow" 118 of image 114 with image portion 113. Similarly, the last four scan lines 122 of image 116 replace leading "shadow" 119 of image 114 with image portion 117. Thus, the "shadows" 118 and 119 are replaced with the images 113 and 117 of the belt and only section 120 of the image 114 is taken as the representative reflectivity of a berry. The result is the elimination of the "shadows" so that a good berry does not appear to be defective.

The output signals from the video camera 22 are normalized and applied to an analog-to-digital converter 128 (FIG. 9) by the processor 26 where the brightness value for each pixel is digitized. A light intensity threshold is set to distinguish pixel values corresponding to the belt, good berries, and defective berries. Pixel values corresponding to the belt and good berries will be higher than pixel values corresponding to defective berries. Additionally, a pixel number threshold is set to determine the presence of a specimen. The converter 128 includes means 130 for storing the digitized brightness value, a graphics signal processor 132 and a look up table 134. The look up table is organized by brightness values and has a separate memory location or cell 136 for each brightness value which is recognized by the system. The look up table is loaded by a known process by which the system learns which brightness values are to be accepted and/or which ones are to be rejected. At each memory location, a bit is stored to indicate whether the particular brightness value is acceptable or not. For example, a zero (0) may indicate that the brightness value is acceptable, and a one (1) may indicate that it is not. The brightness value information for each successive pixel is applied to the look up table as an address vector, and the output of the look up table indicates whether the brightness value of a particular pixel is acceptable. The information in the look up table is then applied to a lateral spatial filter 138 which causes an object on the conveyor belt to be rejected only if it has a certain number or sequence of unacceptable brightness values. This operation is controlled by the processor 26 which interfaces with the other elements in a conventional manner which should be apparent to those skilled in the art.

Figure 9:
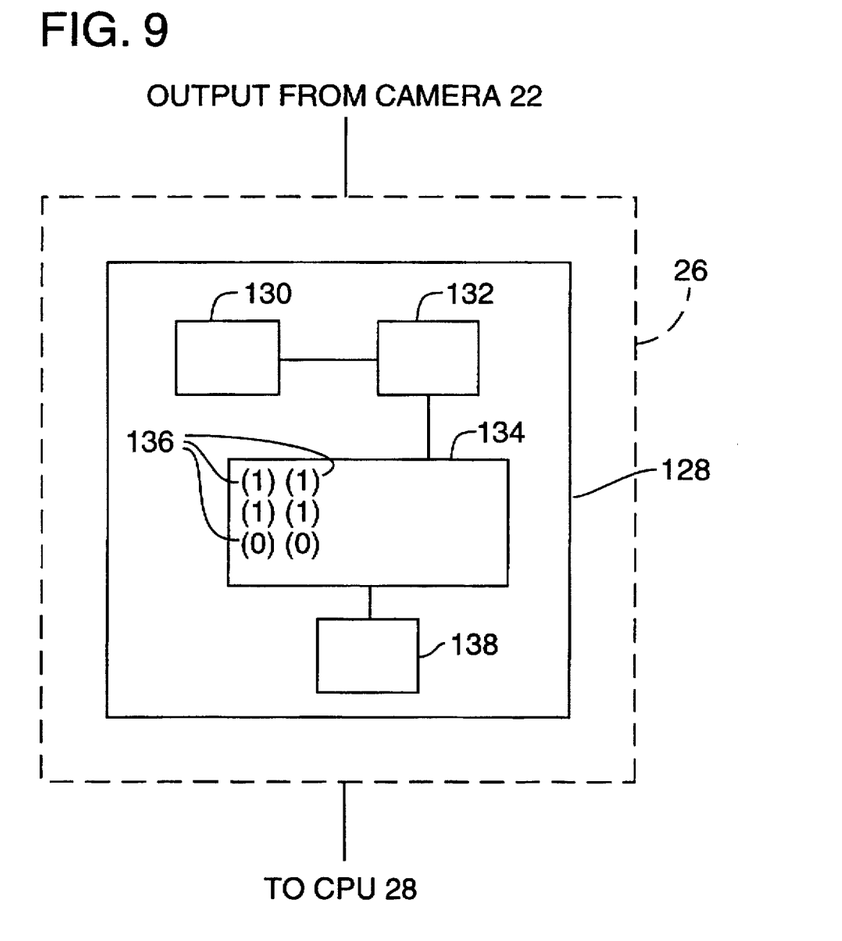
FIG. 9 is a schematic diagram illustrating the sorting processor.
Figure 10:
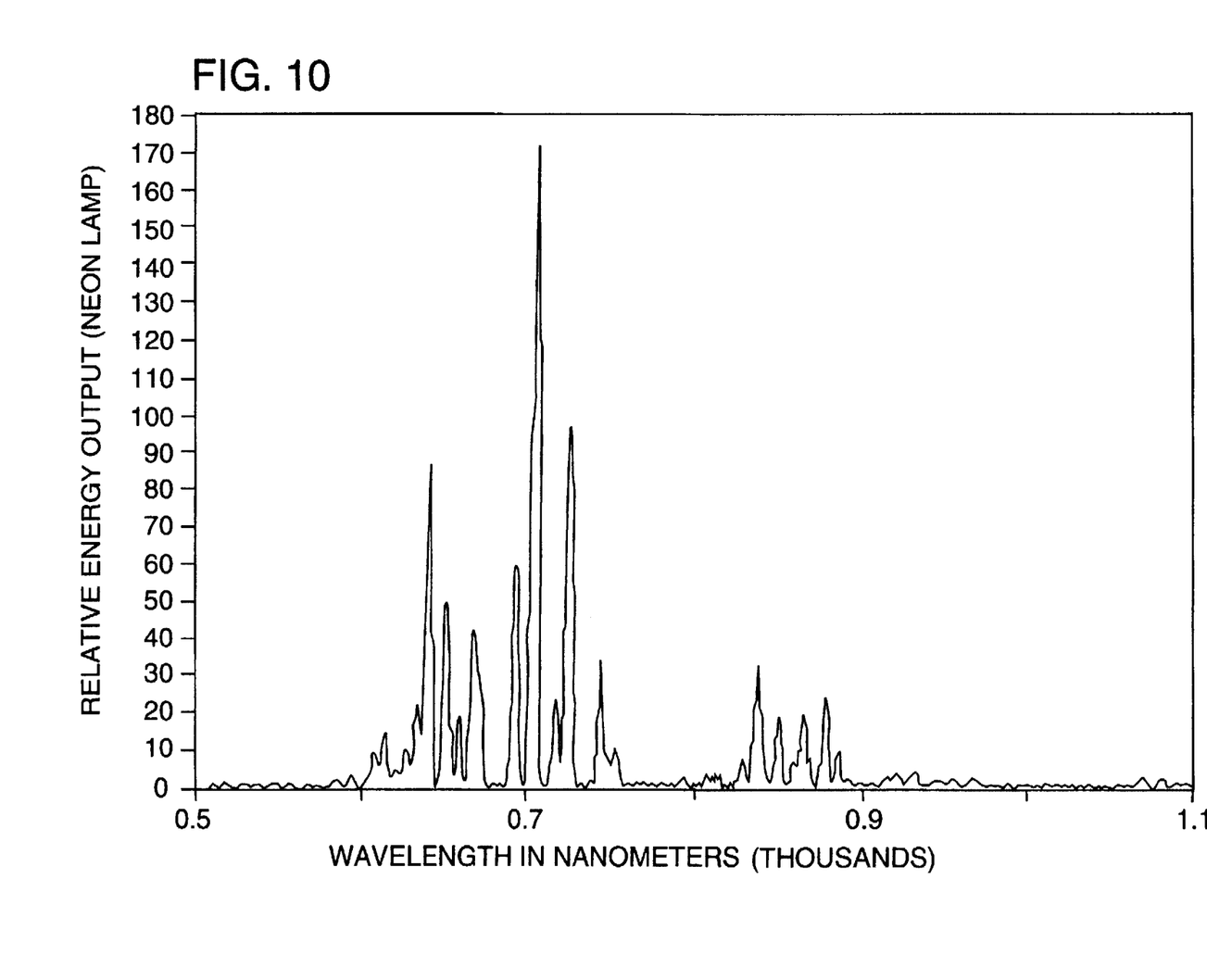
FIG. 10 presents a representation of the relative spectral power distribution of a lamp containing neon.

The specimens that are rejected are those that have an above threshold number of poorly reflected pixels. Each pixel value is first compared with the light intensity threshold. When the processor 26 receives a first value below the light intensity threshold, it totals all subsequent consecutive values below the light intensity threshold within the resolution. If this count exceeds the pixel number threshold, processor 26 determines that there is a defective berry. The CPU 28 then commands rejector unit 30 to remove the defective berry.

Although lamps 36 are preferred sources of the illumination, other sources of illumination in the near infrared can also be effective. Gas discharge lamps with other gas mixtures could be used. Instead of or in addition to gas discharge lamps, the illumination could be provided by one or more lasers. GaAs lasers produce high-intensity emission at about 904 nm and can be tuned to produce emissions at other wavelengths in the near infrared by varying the trapping levels with additions of suitable phosphors. Such lasers would be especially useful with a camera 22 that uses a silicon detector. Moreover, sources that produce illumination in wavelength ranges that extend throughout the entire spectrum can also be effective if, for example, wavelengths outside the near infrared are filtered out by the use of an external filter.

It is to be understood that the optical inspection and sorting system 10 may also be used when it desired to separate good white cranberries for the production of fruit juice from good red cranberries to be sold directly to the consumer. Good berries are defined as those not subject to rot or bacterial infection. This method includes illuminating the mixture of good red and white berries. The good berries are illuminated with radiation having wavelengths extending from the visible range (400 nm–700 nm) to the infrared range (700 nm–1100 nm). The optical response of a specimen 16 can also signify differences in the color of the fruit, such as the difference between red cranberries and white cranberries.

In one embodiment, lamps 36 containing primarily neon emit approximately 17 milliwatts per square cm (centimeter) of radiation having wavelengths of approximately 600 nm (nanometers) to 900 nm with the majority of energy concentrated between 600 nm to 750 nm, measured at the focal plane of target specimens 16. The system 10 may include an illumination source that emits radiation in the visible portion of the spectrum (e.g., 400 nm–700 nm). A line scan camera sensitive to the visible portion of the spectrum may be employed and adjusted so that the reflectivity of good white berries reaches just below the saturation point of the camera. Thus, good white berries are perceived by the camera to have a reflectivity much higher than the good red berries and the belt. The system 10 may then select either the white berries having higher reflectivity or red berries having a lower reflectivity to be separated. Alternatively, two cameras may be used. One camera sensitive to infrared wavelengths may be aligned with or off-set from a second camera sensitive to visible wavelengths. These cameras may use multilayer dichroic reflective or absorptive optical filters to preserve operation in the pre-selected portions of the spectrum.

Whatever the source used to produce the illumination, the effectiveness of the methods of separating selected items 16 from the mixture including good cranberries and defective cranberries depends on the effect in combination with the intensity of the illumination, the spectral power distribution of the illumination, the difference in reflectivities of the cranberries over the wavelength range, the sensitivity of camera 22 over that wavelength range, and the bandwidth of processor 26 and CPU 28. Those factors are balanced to optimize the effectiveness of system 10 in identifying and sorting from the mixture the selected items to be removed.

It will be obvious to those having skill in the art that many changes may be made in the above-described details of the present invention without departing from the underlying principles thereof. In addition, many changes may be made to the details of a system for carrying out a method in accordance with the present invention. For example, illumination system 12 may also comprise multiple video cameras 22, a single light source 36 and hemi-elliptical reflector 48, and light source or sources 36 at various distances and angles from conveyor belt 14. The scope of the present invention should, therefore, be determined only by the following claims.

We claim:

1. A method of separating selected specimens of fruits and vegetables that have been subject to bacteria or rot from a volume based on an amount of reflected light from the volume, comprising:

illuminating the volume with infrared light having a wavelength range; the volume containing acceptable specimens having highly reflective chlorophyll within the wavelength range and unacceptable specimens that have diminished chlorophyll reflectivity within the wavelength range due to rot or bacteria;

establishing a value of reflected light from the volume corresponding to chlorophyll reflectivity of acceptable specimens;

scanning the volume to detect reflected light from the volume;

identifying unacceptable specimens having a diminished chlorophyll reflectivity within the wavelength range that is less than the established value; and separating the unacceptable specimens from the volume.

2. The method of claim 1 wherein the wavelength range of the infrared light is between about 750 nm to about 1100 nm.

3. The method of claim 1 wherein the established value of reflected light is about fifty percent of the light used to illuminate the volume.

4. The method of claim 1 wherein the volume includes acceptable specimens containing highly reflective chlorophyll that reflects fifty percent or more of the light within the wavelength range between about 750 nm to about 1100 nm.

5. The method of claim 1 wherein the volume includes unacceptable specimens having diminished chlorophyll reflectivity due the presence of bacteria or rot that reflects less than about fifty percent of the light within the wavelength range between 750 nm to about 1100 nm.

6. A method of separating selected cranberries that have been subject to bacteria or rot from a volume of cranberries based on an amount of reflected light from the volume, comprising:

illuminating the volume with infrared light having a wavelength range; the volume containing acceptable cranberries having highly reflective chlorophyll within the wavelength range and unacceptable cranberries that have diminished chlorophyll reflectivity within the wavelength range due to rot or bacteria;

capturing plural images of each cranberry represented by pixels;

storing data representative of the plural images of each cranberry in a memory;

reading the data from the memory to misalign the plural images of each cranberry so that only one image portion represents the chlorophyll reflectivity of a cranberry;

establishing brightness values for acceptable pixels and unacceptable pixels of the one image portion;

setting a threshold number of unacceptable pixel values indicative of a cranberry that has been subjected to bacteria or rot;

identifying a defective cranberry by comparing its number of unacceptable pixel values to the threshold number; and separating defective cranberries having a number of unacceptable pixel values that exceed the threshold number.

7. The method of claim 6 wherein the wavelength range of the infrared light is between about 750 nm to about 1100 nm.

8. The method of claim 6 wherein the plural images are a leading image portion, a central image portion, and a trailing image portion.

9. The method of claim 8 wherein the one image portion is the central image portion.

10. A method of separating fruits or vegetables from a volume, comprising:

subjecting the volume with light to illicit an optical response of selected specimens within a specified wavelength range that indicates a presence of bacteria or rot; and separating the selected specimens from the volume.

11. The method of claim 10 wherein the wavelength range is between about 750 nm and about 1100 nm.

12. The method of claim 10 wherein the optical response of the selected specimens is a chlorophyll reflectivity of less than about fifty percent of the light used to illuminate the volume.

* * * * *